United States Patent
Urban et al.

(10) Patent No.: US 12,047,262 B2
(45) Date of Patent: Jul. 23, 2024

(54) METHODS FOR MONITORING A DATA TRANSMISSION, APPARATUSES, AND COMPUTER-READABLE MEDIUMS

(71) Applicant: Siemens Healthcare GmbH, Erlangen (DE)

(72) Inventors: Andreas Urban, Bayern (DE); Jutta Kiesel, Forchheim (DE); Peter Greif, Pinzberg/Gosberg (DE); Ludwig Welker, Eggolsheim (DE); Harald Karl, Fuerth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 17/844,959

(22) Filed: Jun. 21, 2022

(65) Prior Publication Data

US 2022/0417124 A1    Dec. 29, 2022

(30) Foreign Application Priority Data

Jun. 23, 2021   (DE) .................... 10 2021 206 494.9

(51) Int. Cl.
*H04L 43/0811*   (2022.01)
*H04L 43/022*    (2022.01)
(Continued)

(52) U.S. Cl.
CPC ........ *H04L 43/0811* (2013.01); *H04L 43/022* (2013.01); *H04L 43/0829* (2013.01); *H04L 43/12* (2013.01); *H04L 67/12* (2013.01)

(58) Field of Classification Search
CPC ........... A61B 6/032; A61B 6/035; A61B 6/03; A61B 6/56; A61B 6/586; H04L 43/0811;
(Continued)

(56) References Cited

U.S. PATENT DOCUMENTS

| 7,240,251 B2* | 7/2007 | Popescu | H04L 1/24 714/704 |
| 7,519,208 B2* | 4/2009 | Popescu | A61B 6/586 382/128 |

(Continued)

FOREIGN PATENT DOCUMENTS

| CN | 1392740 A | 1/2023 |
| DE | 10245450 A1 | 4/2004 |

(Continued)

OTHER PUBLICATIONS

Natarajan S, Ganz A. SURGNET: An Integrated Surgical Data Transmission System for Telesurgery. Int J Telemed Appl. 2009; 2009:435849. doi: 10.1155/2009/435849. Epub May 26, 2009. PMID: 19503803; PMCID: PMC2688654. (Year: 2009).*

(Continued)

*Primary Examiner* — Dhairya A Patel
*Assistant Examiner* — Alex H. Tran
(74) *Attorney, Agent, or Firm* — Harness, Dickey & Pierce, P.L.C.

(57) ABSTRACT

A method includes moving one or more transmit facility or transmit facilities attached to a first component with regard to at least two receive facilities attached at a fixed position to the second component; and at least one of registering a respective error if an error condition exists for the respective receive facility or modifying an operation of an apparatus comprising the first and a second component if the error condition exists for the respective receive facility, the error condition for the respective receive facility depends on location information relating to at least one of the position of the first component with regard to the second component or orientation of the first component with regard to the second component, and/or at least one of a measure for a receive quality of the signals or data packets received from (Continued)

the transmit facility or from at least one of the transmit facilities.

9 Claims, 4 Drawing Sheets

(51) Int. Cl.
*H04L 43/0829* (2022.01)
*H04L 43/12* (2022.01)
*H04L 67/12* (2022.01)

(58) Field of Classification Search
CPC ..... H04L 43/0829; H04L 43/12; H04L 49/90; H04L 49/9052; H04L 47/30; H04L 1/24; H04L 1/1835; H04L 43/0847; H04L 41/5009; H04L 43/087; G01N 2223/419; G01N 23/046
See application file for complete search history.

(56) References Cited

U.S. PATENT DOCUMENTS

| | | | | |
|---|---|---|---|---|
| 7,860,126 | B2* | 12/2010 | Popescu | A61B 6/56 370/473 |
| 9,859,994 | B2* | 1/2018 | Steffens | H04B 17/27 |
| 10,635,615 | B2* | 4/2020 | Cottam | G06F 13/28 |
| 2002/0196743 | A1 | 12/2002 | Thalanany et al. | |
| 2004/0122968 | A1* | 6/2004 | Schilling | H04L 1/0002 709/233 |
| 2004/0141686 | A1 | 7/2004 | Schilling et al. | |
| 2005/0005206 | A1 | 1/2005 | Popescu | |
| 2007/0242798 | A1 | 10/2007 | Popescu | |
| 2008/0069146 | A1* | 3/2008 | Krumme | H04B 10/801 370/477 |
| 2008/0205446 | A1 | 8/2008 | Popescu et al. | |
| 2015/0163532 | A1* | 6/2015 | Shmueli | H04N 21/2747 386/326 |
| 2021/0314270 | A1* | 10/2021 | Dalmiya | H04L 41/16 |

FOREIGN PATENT DOCUMENTS

| | | | | |
|---|---|---|---|---|
| DE | 10322138 | B3 | 9/2004 | |
| DE | 102005027632 | A1 | 10/2006 | |
| DE | 102005035207 | A1 | 2/2007 | |
| DE | 102012217597 | B4 * | 9/2014 | ............... A61B 6/56 |
| JP | 01221958 | A * | 9/1989 | |
| WO | WO 2005117706 | A1 | 12/2005 | |

OTHER PUBLICATIONS

German Office Action and English translation thereof dated Mar. 17, 2022.
German Decision to Grant and English translation thereof dated Jul. 21, 2022.

* cited by examiner

METHODS FOR MONITORING A DATA TRANSMISSION, APPARATUSES, AND COMPUTER-READABLE MEDIUMS

CROSS-REFERENCE TO RELATED APPLICATION(S)

The present application hereby claims priority under 35 U.S.C. § 119 to German patent application number DE 102021206494.9 filed Jun. 23, 2021, the entire contents of which are hereby incorporated herein by reference.

FIELD

Some example embodiments of the present invention relate to methods for monitoring a data transmission between a first and second component. Some example embodiments of the present invention also relate to apparatuses, such as used in medical imaging, to computer programs and to computer-readable data mediums.

BACKGROUND

In the field of medical imaging, in particular with computed tomography units, but also in other areas of application, it can be necessary to transmit data between components moving relative to one another. Thus for example the imaging x-ray sensors in computed tomography units are typically arranged on a gantry supported rotatably with regard to a base and the data processing or visualization is to be done by components fixed with regard to the base, for example workstation computers or fixed-position image processors.

In principle such a data transmission can take place via sliding contacts for example. However, in order to achieve high data rates with lower maintenance outlay and lower susceptibility to errors, it can be advantageous to use a wireless data transmission instead of this over short distances. The data transmission can be undertaken here for example by radio or generally using radio-frequency technology or via a capacitive coupling.

By using a short-range wireless communication a high data rate and a low susceptibility to errors can be achieved. Also further electronics located in the vicinity will not be disturbed or not be disturbed too much by a short-range communication. It is however possible that, because of the relative movement of transmitters and receivers, receivers that are present will temporarily, for example within a certain range of angles of a gantry, be within an area in which a sufficient signal strength for making robust communication possible cannot be received from any of the transmitters.

SUMMARY

While data loss can be avoided in regular operation, for example by redundant receiving of data packets via a number of receivers arranged at different positions of the gantry, the problem described makes a diagnosis of the apparatus using the data transmission significantly more difficult. If fixed pairs consisting of transmitters and receivers were to be used for wireless communication, a disruption of this wireless communication or an outage of the transmitter or the receiver could be detected very easily, for example by a signal strength, data rate or number of packets successfully received being monitored on the receiver side. For example if one of the said variables falls below a predetermined threshold value, an error counter could be incremented and when a predetermined value is reached by the error counter, a warning can be issued to a user or to service personnel. If however such a procedure were to be used in the method described above, then typically, even in operation that is actually free of errors, a high count rate of such an error counter would occur, since it would always be incremented when one of the receive facilities is moved out of the transmit areas of the transmit facilities.

At least some example embodiments provide a method for monitoring a data transmission improved by comparison with the above method, which in particular when components moving relative to one another between which data is to be transmitted are used, makes robust error detection possible.

According to at least one example embodiment, a method for monitoring a data transmission between a first and second component includes moving one or more transmit facility attached at fixed positions to the first component with regard to at least two receive facilities attached at a fixed position to the second component; and at least one of registering a respective error if an error condition exists for the respective receive facility or modifying an operation of an apparatus comprising the first and second component if the error condition exists for the respective receive facility, wherein the error condition for the respective receive facility depends on (1) location information relating to at least one of the position of the first component with regard to the second component or orientation of the first component with regard to the second component, and (2) at least one of (i) a measure for a receive quality of the signals or (ii) data packets received from the transmit facility or from at least one of the transmit facilities.

According to at least one example embodiment, the method includes sending a sequence of a number of consecutive data packets via the respective transmit facility, wherein the respective data packet comprises sequence information, which describes the position of the respective data packet in the sequence; evaluating a packet loss condition after receipt of a number of data packets by at least one of the receive facilities in each case, the evaluating being based on the sequence information of the received data packets and the pack loss condition indicates that at least one of the data packets of the sequence was not received by any of the receive facilities, wherein on the one hand the error condition when at least one of the packet loss condition is registered or the operation of the apparatus comprising the first and second component is modified.

According to at least one example embodiment, the data packets additionally comprise sender information, the sender information describes from which of the transmit facilities the respective data packet was sent, wherein the packet loss condition is evaluated separately in each case for a number of groups of data packets of which the sender information describes the same transmit facility.

According to at least one example data packets are stored in a buffer, wherein the evaluating evaluates embodiment, data packets received from a respective transmit facility or at least part information of the data packets relating to the sequence information of the received the data packets or part information stored in the first part buffer or the data packets or part information stored in the first and second part buffer upon or after a first test condition existing for testing packet loss condition, the first test condition being based on (i) at least one of a number of the data packets or a total size of the data packets or (ii) part information stored in the part buffer of the buffer.

According to at least one example embodiment, the first component is supported rotatably on the second component or vice versa, wherein an angle of rotation between the first and second component or information correlated with the angle of rotation is the location information.

According to at least one example embodiment, the error condition is only occurs when the angle of rotation lies in a predetermined range of angles of rotation or in one of a number of predetermined ranges of angles of rotation.

According to at least one example embodiment, the error condition only occurs when a subcondition evaluating the location information occurs.

According to at least one example embodiment, the number of the receive facilities used is greater least two more than the number of the transmit facilities by one or at used.

According to at least one example embodiment, an apparatus includes a first component; and a second component, wherein through a change of at least one of a position or an orientation of the first component with regard to the second component one or more transmit facility attached at a fixed position to the first component are each able to be moved with regard to at least two receive facilities attached at a fixed position to the second component; and processing circuitry configured to cause the apparatus to perform the method of claim 1.

According to at least one example embodiment, at least one of (i) the apparatus is configured for use in medical imaging or (ii) the first component includes at least one imaging sensor.

According to at least one example embodiment, the processing circuitry is configured to execute stored instructions.

According to at least one example embodiment, a computer-readable data medium including instructions, when executed by processing circuitry, configured to cause an apparatus to perform a method comprising moving one or more transmit facility attached at fixed positions to a first component with regard to at least two receive facilities attached at a fixed position to a second component, the apparatus comprising the first component and the second component; and at least one of registering a respective error if an error condition exists for the respective receive facility or modifying an operation of the apparatus comprising the first component and the second component if the error condition exists for the respective receive facility, wherein the error condition for the respective receive facility depends on (i) location information relating to at least one of the position of the first component with regard to the second component or orientation of the first component with regard to the second component, and (2) at least one of (i) a measure for a receive quality of the signals or (ii) data packets received from the transmit facility or from at least one of the transmit facilities.

According to at least one example embodiment, data packets received from a respective transmit facility or at least part information of the data packets relating to the sequence information of the received data packets are stored in a buffer, wherein the evaluating evaluates the data packets or part information stored in the first part buffer or the data packets or part information stored in the first and second part buffer upon or after a second test condition existing, the second test condition being based on (i) at least one of a number of the date packets or a total size of the data packets or (ii) part information stored after fulfillment of the first test condition in a further part buffer of the buffer and/or on the other hand depends on a time elapsed since fulfillment of the first test condition.

BRIEF DESCRIPTION OF THE DRAWINGS

Further advantages and details of the invention emerge from the exemplary embodiments given below and the associated figures. In the figures, in schematic diagrams.

DETAILED DESCRIPTION

Figure 1:
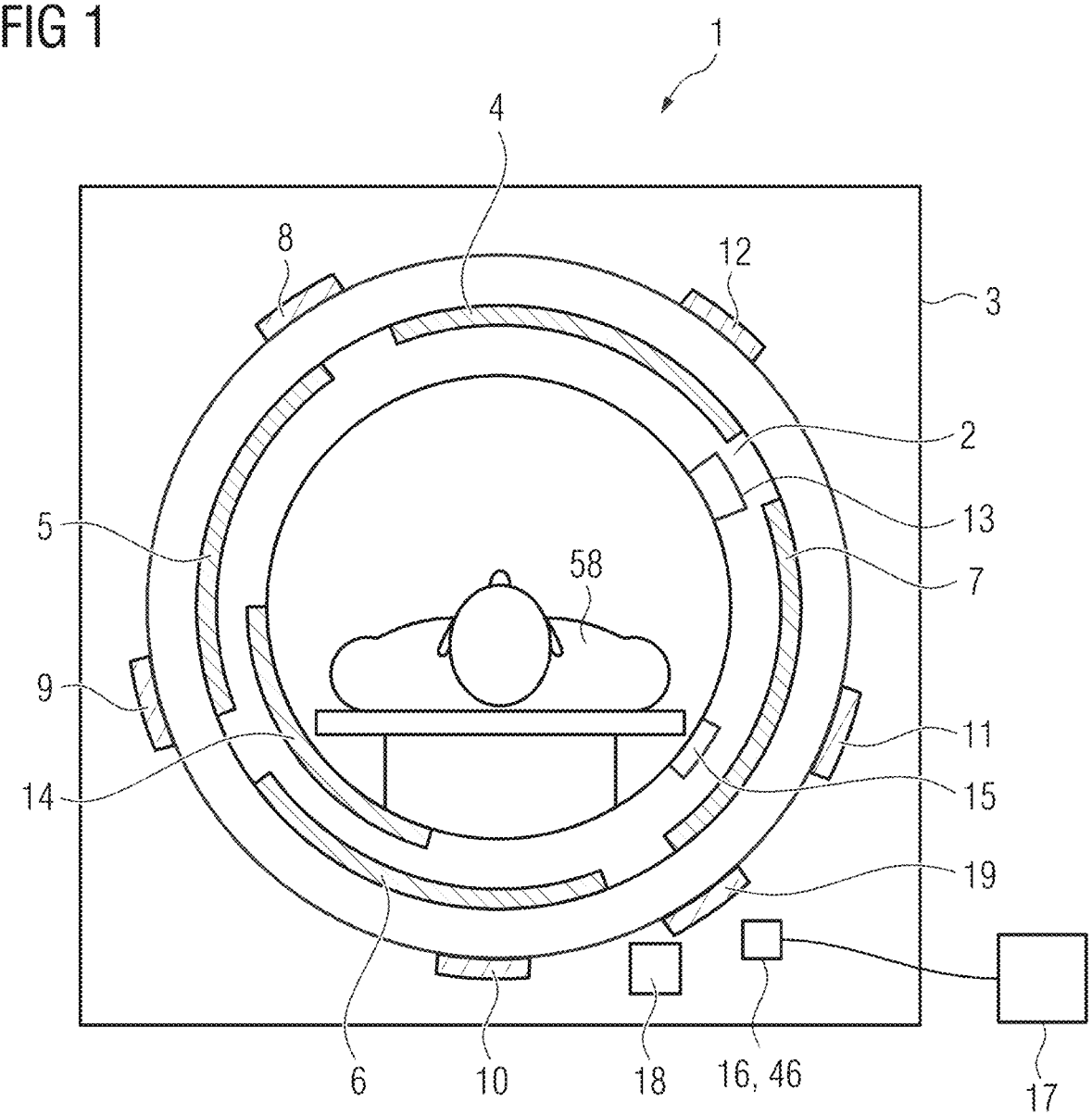
FIG. 1 shows an exemplary embodiment of an inventive apparatus, which is used in the example for medical imaging, and which is configured for carrying out an exemplary embodiment of the inventive method for monitoring a data transmission.

At least one example embodiment provides a method of the type stated at the outset, wherein, on fulfillment of an error condition for the respective receive facility a respective error is registered and/or the operation of an apparatus comprising the first and second component is modified, wherein the fulfillment of the error condition for the respective receive facility depends both on location information determined relating to the position and/or orientation of the first component with regard to the second component and also on a measure for a receive quality of the signals and/or data packets received from the transmit facility or from at least one of the transmit facilities.

Additionally taking into account the location information within the framework of the error condition makes it possible in the inventive method, within the framework of error detection, only to take account of those operating situations in which, due to the relative position of the transmit facilities in relation to the respective receive facility, any sufficient receive quality at all at the receive facility is to be expected during error-free operation. Thus in particular only periods of time can be taken into account for the evaluation of the error condition at which, during error-free operation and with fully-functional transmit and receive facilities, a sufficiently high receive quality is expected. Operating situations in which, due to the relative position or orientation of the components because of the system, a lower receive quality is expected, can remain unconsidered. Thus, in the inventive method, the fulfillment of the error condition points to the actual presence of a fault or a defect and the problems discussed at the start are avoided.

The transmission from the transmit facility to the receive facility can in particular be done wirelessly. As explained above, in this case, through the relative movement of the components, a receive antenna of the receive facility can be moved out of the emission range of the respective transmit facility for example, in which a sufficient signal quality is to be expected. As an alternative for example a wired transmission, for example via a sliding contact, would be possible, wherein the sliding contact is only closed in specific positions or orientations for example. With a rotatable support of the first component on the second component or vice versa for example, such a sliding contact can only be guided over a part of the angle of rotation in the circumferential direction.

The registration of an error can be understood for example as the incrementation of an error counter, in particular of an error counter assigned to the respective receive facility. As an alternative or in addition it is also possible for an error to be registered by a corresponding entry, in particular with an assigned time stamp, being written into a log file or similar.

The modification of the operation of the apparatus can serve to issue a warning to a local user or, for example via the Internet or a mobile radio protocol, to a remote user or a server. It is however also possible to stop the operation of the apparatus at least partly, directly or for example when a certain error count or frequency is reached, i.e. for example to prevent a rotation of a component, to switch off an x-ray tube or similar. This can be expedient, since severe disruptions of the data transmission can potentially lead to a loss of data, whereby, for example in the field of medical imaging, it can be expedient to abort an examination and thus for example avoid an unnecessary input of x-ray radiation into an examination object.

Via the respective transmit facility a sequence of a number of consecutive data packets can be sent, wherein the respective data packet comprises sequence information that describes the position of the respective data packet in the sequence, wherein after receipt of a number of data packets by at least one of the receive facilities in each case, a packet loss condition is evaluated, the fulfillment of which depends on the sequence information of received data packets and indicates that at least one of the data packets of the data sequence was not received by any of the receive facilities, wherein on the one hand the error condition is only able to be fulfilled on fulfillment of the packet loss condition and/or wherein on the other hand, on fulfillment of the packet loss condition, a packet loss is registered and/or the operation of the apparatus comprising the first and second component is modified.

Through the additional evaluation of the packet loss condition on the one hand a significantly more robust detection of errors or faults during the data transmission is made possible and on the other hand additional diagnostic information is obtained, which can make it possible for example to localize defects.

If for example simple error counters are used, which however, as explained above, by taking account of the location information for example, are not incremented in specific relative orientations of the components to one another, the potential problem that occurs here is that for example due to a restricted granularity of the location information, for implementation reasons the areas in which no error detection is to take place can only be defined relatively roughly. In this case it would either have to be taken into consideration that high error count rates would still occur even during undisturbed operation, which, as explained above, makes error detection significantly more difficult, or it would have to be taken into consideration that specific errors actually occurring would be masked. Moreover it cannot be detected by isolated error counters for individual receive facilities whether for example a data packet, during the receipt of which at a specific receive facility an error has occurred, has been correctly received via another receive facility.

Both disadvantages can be avoided by additional evaluation of a packet loss condition. For example data packets sent by a respective transmit facility can be numbered sequentially. It can thus be easily recognized when gaps occur in the sequence. The sequence information can be added to the data packet for example by the transmit facility itself, for example as a consecutive number, or it can already be added before the transfer to the transmit facility, by a router for example, to the packets to be transmitted, distributed to different transmit facilities.

As will be explained in greater detail further on, within the framework of the evaluation of the packet loss condition in particular, packets received from all receive facilities can be aggregated. While this makes possible a robust detection of whether a data packet has actually been received by one of the receive facilities, in the event of a packet loss it is however not possible to detect or at least not to detect without a significant outlay in time where in the system a fault has occurred. Therefore it is especially advantageous to combine the evaluation of the packet loss condition and the combined evaluation of the measure for the receive quality and of the location information explained above, in order to assign faults that actually lead to packet losses specifically to a particular receive facility or for example in order to only consider an error detected at a receive facility as critical and thus to count it when it actually leads to a lost packet.

Here it is possible to test the error condition and the packet loss condition separately first of all and to acquire errors and packet losses, for example by separate counters, separate log files or also in a common log file. The error diagnosis for an apparatus used within the framework of the data transmission or an apparatus implementing the data transmission can then be done by evaluation of corresponding counters or files in a downstream process. It can be advantageous however to monitor the two criteria jointly and thus to use an error condition that additionally evaluates the packet loss condition.

The inventive method, in particular the evaluation of the error and/or packet loss condition, can be implemented for example by a correspondingly programmed data processing facility, i.e. can in particular be a computer-implemented method. As an alternative the corresponding processing steps can be implemented for example by hard wiring or by an ASIC.

The data packets can additionally comprise sender information, which describes the transmit facilities from which the respective data packet was sent, wherein the packet loss condition is evaluated in each case separately for a number of groups of data packets, of which the sender information describes the same transmit facility. The sender information can be added to the respective data packet by the transmit facilities themselves or for example by a router, which distributes the data packets to the different transmit facilities. By evaluation of the sender information it can be easily identified for example when the packet loss condition is fulfilled, because a specific transmit facility is defective or especially susceptible to faults. Such information is highly relevant within the framework of the diagnosis, since for example it can indicate that maintenance is required or can greatly facilitate maintenance, since it is already known which component is defective or especially susceptible to faults.

Moreover the additional taking into account of the sender information makes it significantly easier to recognize whether all data packets of a sequence have been received. If a number of transmit facilities are used, these can namely send different data packets simultaneously or at least overlapping, so that, under some circumstances, a unique packet sequence cannot be determined. If the data packets transmitted by the different transmit facilities are considered separately for the individual transmit facilities however, a clear sequence results and thus a simple identification of the individual data packets, for example by a sequence number.

Data packets or at least the part information of the data packets relating to the sequence information of the data packets received from a respective transmit facility can be stored in a buffer, wherein in each case, on or after fulfillment of a first test condition, the fulfillment of which depends on a number and/or a total size of the data packets or part information stored in a part of the buffer, or on or after fulfillment of a second test condition, the fulfillment of which on the one hand depends on a number and/or a total size of the data packets or part information stored in a further part of the buffer after fulfillment of the first test condition and/or on the other hand depends on a time elapsed since fulfillment of the first test condition, the data packets or part information stored in the first part buffer or the data packets or part information stored in the first and second part buffer is evaluated for testing the packet loss condition.

A buffering of the data packets or part information in a buffer already enables it to be checked with little effort whether the sequence information stored there indicates gaps, for example because, with a sequential packet numbering of the data packets, specific packet numbers are missing.

The approach whereby already with sufficient filling of a part buffer, i.e. on fulfillment of the first test condition, the packet loss condition can be evaluated immediately at this part buffer, has its limits however, when due to different transmission paths, in particular due to the receipt by different receive facilities, data packets can be received in a different order than the one in which they were sent. In this case it can be advantageous, after fulfillment of the first test condition, additionally to take account of data packets arriving, which could potentially fill gaps still present in the first part buffer and thus, as explained above, to use a second test condition and only on or after fulfillment of this second test condition, to take account of data packets or part information from both part buffers within the framework of the packet loss condition.

A relatively simple option for realizing the process described is to use an alternating buffer, so that received data packets, in particular received data packets that originate from a specific transmit facility, regardless of the receive facility via which they were received, are first written into the first part buffer wherein, at a certain occupancy level or a certain number of entries in this buffer, there is a switch to the second part buffer, into which data packets received after fulfillment of the first test condition are written. Somewhat later, i.e. on fulfillment of the second test condition, the data stored in the first part buffer together with the data going beyond this stored in the second part buffer can be evaluated jointly. The writing of additional data packets does not have to be interrupted for this and the first test condition can for example be fulfilled once again when the second part buffer is sufficiently filled, after which once again there is a switch to the first part buffer, which stores the further data packets until the second test condition is fulfilled. Instead of the totality of data packets naturally only part data of the respective data packets can be stored in the respective part buffer, as has already been explained above.

The first component can be supported rotatably on the second component or vice versa, wherein the angle of rotation between the first and second component or information correlated with this angle of rotation is used as location information. In particular the relative position and orientation of the first and second component according to the angle of rotation of 360° can thus correspond to the position and orientation at an angle of rotation of 0°. The angle of rotation can be detected for example using an angle of rotation sensor, for example a Hall sensor, or can be known for example due to a corresponding actuation of an actuator, which moves the components relative to one another.

The error condition can then exclusively be able to be fulfilled when the angle of rotation lies in a predetermined range of angles of rotation or in one or more predetermined ranges of angles of rotation.

In general the error condition can only be able to be fulfilled when a subcondition evaluating the location information is fulfilled. The subcondition or the predetermining of at least a range of angles of rotation can thus serve as a type of filter for the fulfillment of the error condition and for example the incrementation of an error counter can be suppressed when the angle of rotation does not lie in any of the predetermined ranges of angles of rotation or the subcondition is not fulfilled.

The predetermined range of angles of rotation or the predetermined ranges of angles of rotation can in particular be different from one another for at least one pair of receive facilities, meaning that for specific angles of rotation the fulfillment of the error condition is only impossible for parts of the receive facilities or only for one of the receive facilities. Independently of this, for each receive facility, in particular precisely as many ranges of angles of rotation can be defined as there are transmit facilities available. In particular precisely those ranges of angles of rotation are predetermined, in which, according to expectations, a signal with sufficient quality should be able to be received from at least one transmit facility.

The number of receive facilities used can be greater than the number of transmit facilities used by precisely one or at least two. The transmit and receive facilities could be distributed in this way to the first and second component, for example along the circumferential direction of a rotatably supported component, so that a signal or data packet emitted by a transmit facility can be received in regular operation without faults by at least one of the receive facilities. A receipt of a data packet sent by a number of the receive facilities is typically unproblematic, since data packets received multiple times can be recognized, for example on the basis of the sequence information or due to other information contained in the data packet, and thus duplicates can be discarded.

As well as the inventive method, example embodiments of the present invention relates to an apparatus with a first and second component wherein, by changing a position and/or an orientation of the first component with regard to the second component, one or more transmit facility or transmit facilities attached at a fixed position to the first component are able to be moved in each case with regard to at least two receive facilities attached at a fixed position to the second component, wherein the apparatus comprises means that are suitable for carrying out the inventive method. In particular the apparatus comprises, as means or as part of the means, a data processing facility, which is configured or programmed to evaluate the error condition. In addition or as an alternative the data processing facility can be configured or programmed to evaluate the packet loss condition.

The location information can be acquired by sensors, for example using an angle of rotation sensor, but can also be known however by the data processing facility or a control facility of the apparatus controlling at least one actuator, which predetermines the movement or the change of orientation between the components. Then, starting from a defined or acquired initial setting, the setting at that moment can be determined on the basis of control information.

The means can be multipart and for example comprise a respective data processing facility for the first and second component. The data processing facility of the first component can be configured or programmed to undertake a distribution of data to be sent to data packets, to distribute these data packets to the transmit facilities and/or to add information to the data packets, in particular sequence information or transmitter information. A data processing facility configured or programmed in this way can form the router discussed above. The data processing facility of the second component can in particular serve to check the error or packet loss condition.

The second component can be a fixed base, on which the first component is supported movably, in particular rotatably, or vice versa. The movement path of the transmit facilities with regard to the second component can in particular be cyclical, i.e. repeat itself after a particular movement distance or a specific angle of rotation. This is the case for example with a rotatable support of the second component on the first component or vice versa.

The apparatus can be used for medical imaging and in particular can be a computed tomography unit. In addition or as an alternative the first component can bear at least one imaging sensor, for example an x-ray detector. Image data of the imaging sensor can be transmitted as data packets via the transmit facilities. In particular a router can be connected between the sensor and the transmit facilities, which distributes the data to the different transmit facilities. It can be sufficient here to route each data packet to precisely one transmit facility for transmission, in order to achieve that no data packet gets lost during orderly operation despite the relative movement of the components.

Example embodiments of the present invention moreover relate to a computer program, comprising commands that cause the inventive apparatus to carry out the inventive method. In particular the computer program serves to program means of the apparatus, i.e. in particular at least one data processing facility.

Example embodiments of the present invention moreover relate to a computer-readable data medium, on which an inventive computer program is stored.

FIG. 1 shows an apparatus 1 with a first and second component 2, 3, which are movable, in the example rotatable, relative to one another and between which a data transmission is to take place. In the example the apparatus is used for medical imaging, wherein a computed tomography unit is shown by way of example. Thus, in this example image data of the examination object 58 is acquired, by x-ray radiation being emitted via an x-ray tube 13 that, after passing through the examination object 58, is detected by the imaging sensor 14, which in the example is an x-ray detector.

The resulting image data is to be provided to an external facility 17. Since however the component 2 that bears the imaging sensor 14 is supported movably, in the example rotatably, with regard to the component 3 that bears a data processing facility 16, which is to provide the data to the external facility 17, a data transmission is required between components supported movably in relation to one another. This is implemented in the example by the image data being divided first of all by a router 15 into a number of data packets, wherein for each of the data packets one of a number of transmit facilities 4, 5, 6, 7 available is selected, via which this data packet is to be emitted wirelessly.

By more receive facilities 8-12 being available than transmit facilities and a suitable distribution of the transmit and receive facilities 4-12 being selected it can be achieved that always at least one of the receive facilities 8-12 can receive signals or data packets emitted by a respective transmit facility 4-7. The data packets received by the different receive facilities 8-12 are merged by the data processing facility 16, wherein in particular data packets received multiple times can be sorted out, and forwarded to the external facility 17.

In the field of medical imaging in particular it should be rapidly detected when, due to an external fault or a defect of one of the transmit or receive facilities 4-12 for example, the data transmission is disrupted, which under some circumstances can lead to a loss of packets and thus for example to unusable measurements.

If the transmit facilities 4-7 were each to have a fixed assignment to one of the receive facilities 8-12, a fault or a defect of a specific channel, meaning of a specific pair of transmit and receive facilities 4-12, could be recognized relatively easily by a measure for a receive quality being determined, for example a signal amplitude or a packet loss rate of the individual receive facility 8-12, and with receive quality that is too poor, i.e. for example when the measure falls below a threshold value, an error is registered or due to this error the operation of the apparatus 1 is modified, for example the x-ray tube 13 is deactivated or similar.

Since, due to the relative movement of transmit and receive facilities 4-12, individual receive facilities 8-12 however temporarily do not receive a signal or only receive a signal with very poor quality from any of the transmit facilities 4-7, a procedure of this type would already register errors even in actually fault-free operation.

Therefore another method is used for error detection, which will be explained below in greater detail with additional reference to FIG. 2. The relevant elements shown for the component 2 correspond here, apart from their greatly simplified representation, to the elements already shown with regard to FIG. 1. However for the component 3 the further processing of the data packets received by the receive facilities 8-12 is shown by a number of function blocks, which are implemented by means 46 of the apparatus, in the example likewise the data processing facility 16.

Here an error condition 21-25 is evaluated separately first of all for each of the receive facilities 8-12. The respective error condition 21-25 depends on the one hand on a measure for a receive quality of the signals or data packets received by the respective receive facility 8-12 from the transmit facilities 4-7. In order however to avoid the problems described above, that exclusively taking into account such a measure would mean that, even with error-free functioning of the apparatus 1, such an error condition would frequently be fulfilled, the respective error condition 21-25 additionally evaluates location information 20, which relates to the position or in the example the orientation of the first component 2 with regard to the second component 3. In the example a relative angle of rotation of the first component 2 with regard to the second component 3 is detected by an angle of rotation sensor 19. As an alternative or in addition it would also be possible for example to determine such an angle of rotation from control signals of the data processing facility 16 for controlling an actuator 18 for rotating the component 2 or similar.

An example for the evaluation of the error conditions 21-25 will be explained in greater detail below with additional reference to FIG. 3 for the error condition 21. Here FIG. 3 shows three diagrams with the same x axis, on which the location information 20, i.e. in the example the angle of rotation 41 of the component 2 with regard to the component 3, is plotted.

In the uppermost diagram the y axis represents the measure 26 for the receive quality, i.e. for example a signal strength of the received signal or a signal-to-noise ratio. The curve shown shows an example of a graph of this measure 26 for one revolution of the component 2. It can be seen here that the measure 26 for the receive quality of the receive facility 8 falls away sharply in each case when the receive facility 8, due to the rotation of the component 2, is located in an area between two transmit facilities 4-7 viewed in the circumferential direction of the component 2. The reduction of the measure 26 for the receive quality in the time intervals 27, 28, 29 and 30 is thus inherent in the system and is not to be recognized as an error.

In the example additional falls in the measure 26 for the receive quality are indicated in the time intervals 32 and 33 that are not produced by the system geometry and could have been caused for example by external faults or defects at the receive facility 8 or at the transmit facility 8-12. In these time intervals 32, 33 an error should thus be detected in order to make a diagnosis possible.

Figure 3:
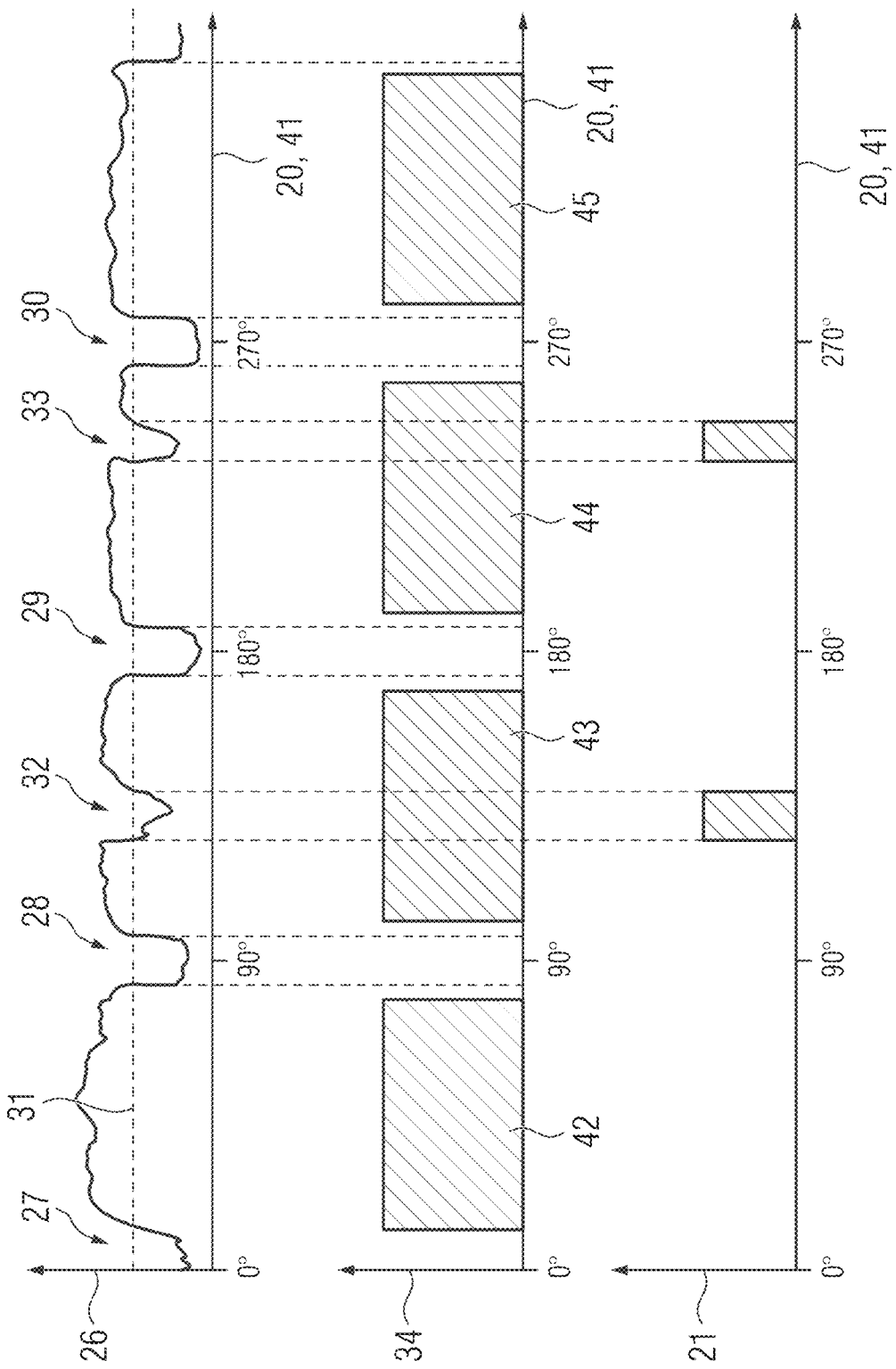
FIG. 3 shows diagrams for evaluation of an error condition in the exemplary embodiment of the inventive method.

In order to achieve this an error condition 21 is used, which is only then able to be fulfilled at all when a subcondition 34 is fulfilled, which, as is shown schematically in the middle diagram of FIG. 3, is fulfilled precisely when the angle of rotation 41 lies in one of the marked angle of rotation ranges 42, 43, 44 or 45.

As a further subcondition that must be fulfilled in order for the error condition to be fulfilled, an undershooting of the threshold value 31 by the measure 26 for the receive quality is required. This leads, as is shown schematically in the lowest diagram in FIG. 3, to the error condition 21 exclusively being fulfilled in the time intervals 32 and 33 and not in the time intervals 27, 28, 29 and 30, i.e. to the desired behavior.

In principle the evaluation of the error conditions 21-25 for diagnosis or control purposes is already sufficient. Here however it would be problematic that, depending on choice of the extent of the angle of rotation ranges 42-45, either specific errors will not be detected or errors will continue to be detected under some circumstances when actually there is no error occurring. Moreover, with the use of relatively simple approaches to the evaluation of the fulfillment of the error condition, i.e. for example when an error counter is incremented each time that the error condition is fulfilled, it cannot be readily recognized whether an error has been created by a specific one of the transmit facilities 4-7 for example.

Figure 2:
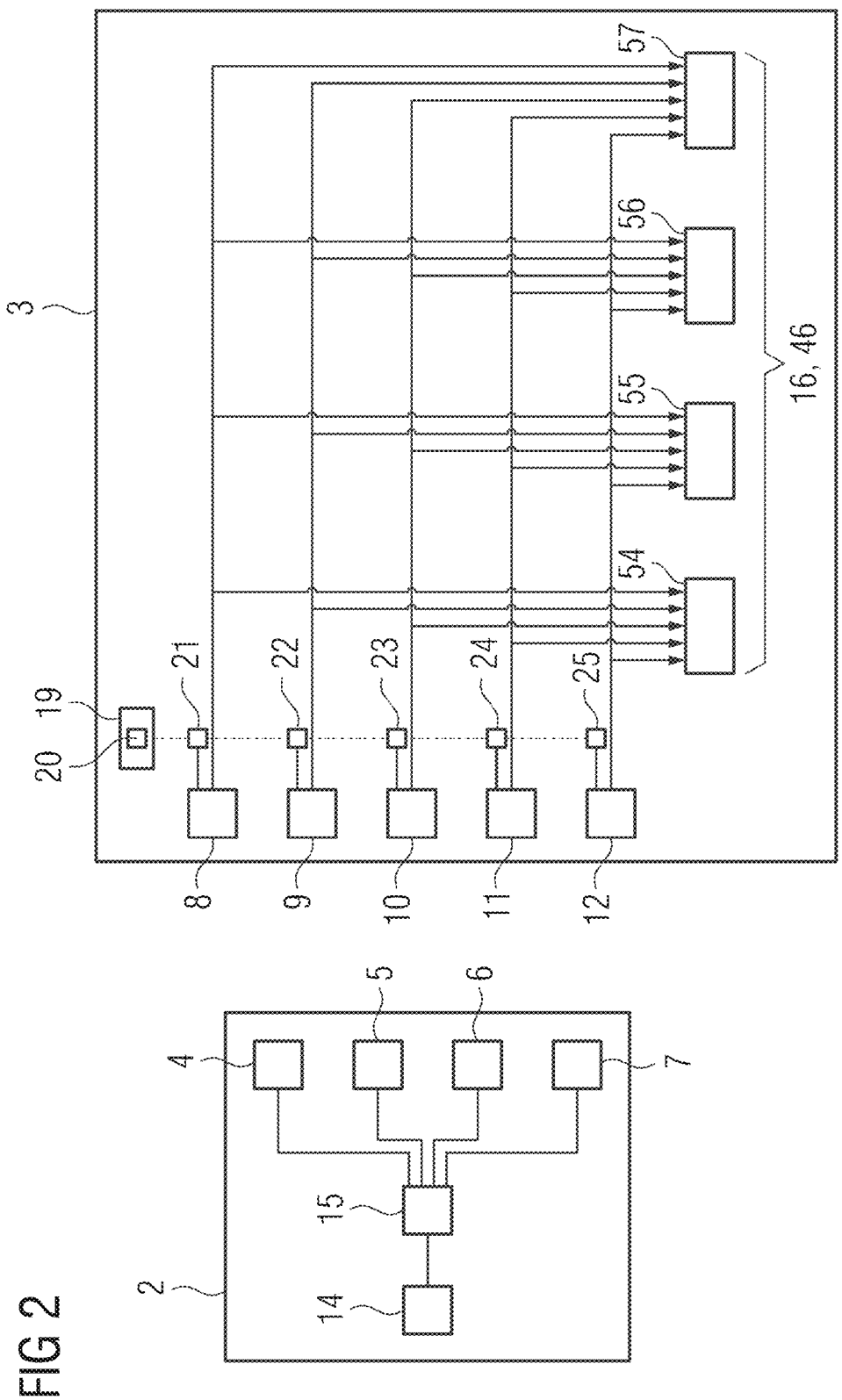
FIG. 2 shows a diagram of the elements relevant for monitoring the data transmission in FIG. 1.

Thus, for further improvement of error monitoring, in the example shown in FIG. 2, the packet loss conditions 54-57 are additionally evaluated. Here the packet loss condition 54 checks a loss of packets of the transmit facility 4, the packet loss condition 55 a loss of packets of the transmit facility 5, the packet loss condition 56 the loss of packets of the transmit facility 6 and the packet loss condition 57 the loss of packets of the transmit facility 7.

Thus it can be uniquely established whether a packet loss and thus an actual error has occurred or not. Since moreover the error conditions 21-25 are evaluated, with a receive-side cause of an error, by contrast with an exclusive evaluation of packet losses it can readily uniquely be recognized for which of the receive facilities 8-12 errors are occurring.

Figure 4:
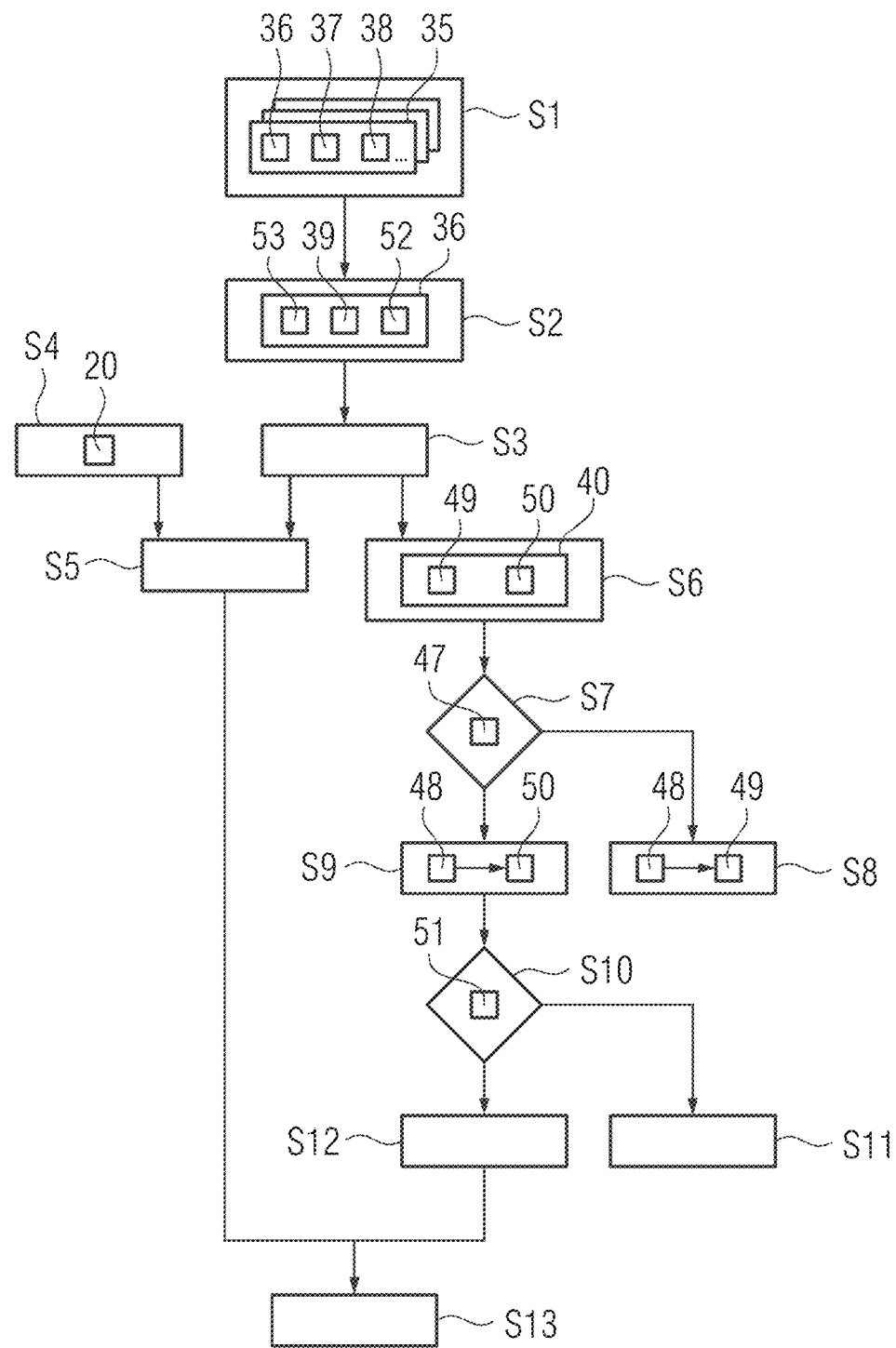
FIG. 4 shows a flow diagram of the exemplary embodiment of the inventive method.

A concrete implementation of the evaluation of the packet loss condition 54-57 within the framework of a method for monitoring a data transmission will be explained bellow with regard to the flow diagram of such a method shown schematically in FIG. 4.

In step S1 the image data provided by the imaging sensor 14 is divided up by the router 15 into a number of sequences of consecutive data packets 36-38, wherein a separate sequence 35 is provided for each of the transmit facilities 4-7. In particular each data packet to be transmitted here can only be contained in precisely one of the sequences 35.

In step S2 the respective data packet, as is shown schematically for the data packet 36, is supplemented by additional information. This can be done by the router 15 or by the respective transmit facility 4-7 used to send it. As well as the user data 52 provided in the example by the sensor 14, the data packet 36-38 comprises sequence information 39, which describes the position of the respective data packet in the sequence 35. For example a counter can be incremented by 1 for each data packet and stored as sequence information 39 in the respective data packet 36-38. In addition sender information 53 is added into the respective data packet 36-38, which describes from which of the transmit facilities 4-7 the respective data packet is being sent.

In step S3 the correspondingly supplemented data packets 36-38 of the respective sequence 35 are sent by the respective transmit facility 4-7 and, provided no faults occur, are received by at least one of the receive facilities 8-12. Simultaneously with the sending of a respective data packet 36-38 by a respective transmit facility 4-7, in step S4 the location information 20 is acquired, in order subsequently, in step S5, as already explained above, to evaluate the respective error condition 21-25 for the respective receive facility 8-12.

In step S6 the data packets 36-38 received by the different receive facilities 8-12 are aggregated and sorted into separate groups in accordance with the transmitter information 53 stored in them, wherein the following steps will only be explained for one of these groups by way of example.

The data packets 36-38 of a group or at least a respective item of part information 48 of each data packet 36-38 of the group, which comprises at least the sequence information 39, should be held in a buffer 40, which is formed by the two part buffers 49 and 50, wherein the part buffers 49 and 50 can in particular be used as alternating buffers.

To this end, in step S7, first of all a first test condition 47 is tested, the fulfillment of which depends on the number or total size of the data packet or part information 48 already held in the part buffer 49. In particular this first test condition can be fulfilled when the first part buffer 49 is completely filled. If this is not the case, then, in step S8 the part information 48 or the data packet 36-38 can be written into the part buffer 49, whereby the evaluation of the respective packet loss condition 54-57 initially, until such time as a further data packet of the corresponding group is received, is concluded.

If the first test condition 47 is fulfilled on the other hand, then in step S9 the part information 48 is written instead into the part buffer 50 and subsequently, in step S10, a second test condition 51 is evaluated, the fulfillment of which depends on the number or total size of the data packets held in the part buffer 50 after fulfillment of the first test condition 47. As an alternative or in addition a fulfillment of the second test condition can also depend on a time that has elapsed since fulfillment of the first test condition 47.

If the second test condition 51 is not fulfilled, then the evaluation of the respective packet loss condition 54-57 in step S11 is interrupted until such time as a further data packet 36-38 of the respective group is received. To put it another way, the evaluation of the second test condition 51 serves, after fulfillment of the first test condition 47, to wait for a certain time or for a certain number or a certain size of received packets and only on fulfillment of the second test condition 51, in step S12, to check the data packets 36-38 or part information 48 held in the buffer 40 or in the part buffers 49, 50 in order to detect a packet loss.

Since the stored data packets 36-38 or part information 48 comprise the sequence information 39, it can be checked for example whether for each data packet 36-38, the part information or its part information 48 is stored in the part buffer 49, a data packet 36-38 or part information 48 with the immediately following sequence information 39 is stored in the buffer 40, i.e. in the part buffer 49 or in the part buffer 50. If this is the case, then at least during the time interval during which information is being written into the part buffer 49, no packet loss is occurring. On the other hand, if this is not the case, a packet loss can be assumed, at least when it is ensured that sufficiently many received packets or sufficient time lie between the fulfillment of the first and second test condition 47, 51.

Thus it can be decided in step S12 whether the respective packet loss condition 54-57 is fulfilled for the respective sequence 35 of data packets 36-38 or the respective transmit facility 4-7 or not. Moreover, for subsequent passes the role of the part buffer 49 and 50 can be swapped so that first of all, on non-fulfillment of the first test condition data continues to be written into the part buffer 50 and only after this is there a switch back to the part buffer 49.

In step S13 the result of the evaluation of the error conditions 22-25 in step S5 and the result of the evaluation of the packet loss conditions 54-57 in step S12 are processed jointly. As an alternative it would also be possible for example initially to evaluate corresponding data separately, for example in separate log files or using separate error counters and only carry out a summary group analysis subsequently.

The joint processing in step S13 can serve for example to provide an informative log file, which can already contain information as to whether counted errors or a packet loss detected has been created by specific transmit facilities 4-7 or specific receive facilities 8-12 or whether such an assignment is not possible.

A joint processing is especially expedient when an intervention is to be made into the operation of the apparatus 1, since for example, on detection of an individual packet loss, it can be sufficient to send this packet once again, while for example a joint occurrence of individual packet losses with a high value of an error counter, which is incremented on fulfillment of a specific one of the error conditions 21-25, can actually point to a defective receive facility 8-12, which is why in this case for example a further operation of the apparatus 1 can be prevented until maintenance of it has been undertaken.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/ or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been illustrated and described in greater detail by example embodiments, the present invention is not restricted by the disclosed examples and other variations can be derived herefrom by the person skilled in the art without departing from the scope of protection of the present invention.

The invention claimed is:

1. A method for monitoring a data transmission between a first component and a second component, the method comprising:

moving one or more transmit facilities with respect to at least two receive facilities, the one or more transmit facilities being attached to the first component at a fixed position and the at least two receive facilities being attached to the second component at a fixed position, and the moving being a change in at least one of a position or an orientation of the one or more transmit facilities;

sending a sequence of a number of consecutive data packets via a respective transmit facility of the one or more transmit facilities, each respective data packet of the sequence including sequence information, and the sequence information describing the position of the respective data packet in the sequence;

evaluating a packet loss condition of a number of data packets received by at least one of the at least two receive facilities, the evaluating being based on the sequence information of the number of data packets and the packet loss condition indicating that at least one of the data packets of the sequence was not received by any of the at least two receive facilities; and at least one of registering a respective error for the respective receive facility in response to an error condition or modifying an operation of an apparatus including the first and second component for the respective receive facility in response to the error condition, wherein the error condition for the respective receive facility is based on (1) location information relating to at least one of the position of the first component with regard to the second component or the orientation of the first component with regard to the second component, and (2) at least one of (i) a measure for a receive quality of a signal or (ii) the number of data packets received from the respective transmit facility or from at least one of the one or more transmit facilities, the error condition exists when at least one of the packet loss condition is registered or the operation of the apparatus including the first and second component is modified, the number of data packets received from the respective transmit facility are stored in a buffer or the sequence information included in the number of data packets is stored in the buffer, the buffer including a first part buffer and a second part buffer and the number of data packets or the sequence information being stored in the first part buffer until the first part buffer reaches a threshold occupancy and then being stored in the second part buffer, and wherein the evaluating evaluates the number of data packets or the sequence information stored in the first part buffer upon or after a first test condition existing for testing packet loss condition, the first test condition existing when the first part buffer is full, the first part buffer being full being based on at least one of (i) at least one of a number of the number of data packets stored in the first part buffer or a total size of the number of data packets stored in the first part buffer or (ii) the sequence information stored in the first part buffer, and the evaluating further evaluates the number of data packets or the sequence information stored in the first part buffer and the second part buffer upon or after a second test condition existing for testing packet loss condition and after the first test condition existing for testing packet loss condition, the second test condition occurring upon either an elapsed time since the first test condition or at least one of (i) at least one of a number of the number of data packets stored in the second part buffer or a total size of the number of data packets stored in the second part buffer before the elapsed time since the first test condition or (ii) the sequence information stored in the second part buffer after the first test condition existing before the elapsed time since the first test condition.

2. The method as claimed in claim 1, wherein each respective data packet of the sequence includes sender information, the sender information describing a transmit facility of the one or more transmit facilities the respective data packet was sent from, the packet loss condition for a first group of data packets is evaluated separately from a second group of data packets based on the sender information of the first group of data packets and the sender information of the second group of data packets describing the same transmit facility.

3. The method as claimed in claim 1, wherein the first component is supported rotatably on the second component, and an angle of rotation between the first and second component is the location information or information correlated with the angle of rotation is the location information.

4. The method as claimed in claim 3, wherein the error condition occurs when the angle of rotation lies in a range of angles of rotation or in one of a number of ranges of angles of rotation.

5. The method as claimed in claim 1, wherein the error condition occurs when a sub condition evaluating the location information occurs.

6. The method as claimed in claim 1, wherein a number of the at least two receive facilities is greater than a number of the one or more transmit facilities.

7. An apparatus for monitoring a data transmission between a first component and a second component, the apparatus comprising:

a first component;

a second component;

processing circuitry configured to cause the apparatus to move one or more transmit facilities with respect to at least two receive facilities, the one or more transmit facilities being attached to the first component at a fixed position and the at least two receive facilities being attached to the second component at a fixed position, and the move being a change in at least one of a position or an orientation of the one or more transmit facilities;

send a sequence of a number of consecutive data packets via a respective transmit facility of the one or more transmit facilities, each respective data packet of the sequence including sequence information, and the sequence information describing the position of the respective data packet in the sequence;

evaluate a packet loss condition of a number of data packets received by at least one of the at least two receive facilities, the evaluating being based on the sequence information of the number of data packets and the packet loss condition indicating that at least one of the data packets of the sequence was not received by any of the at least two receive facilities; and at least one of register a respective error for the respective receive facility in response to an error condition or modify an operation of the apparatus including the first and second component for the respective receive facility in response to the error condition, wherein the error condition for the respective receive facility is based on (1) location information relating to at least one of the position of the first component with regard to the second component or orientation of the first component with regard to the second component, and (2) at least one of (i) a measure for a receive quality of a signal or (ii) the number of data packets received from the respective transmit facility or from at least one of the one or more transmit facilities, the error condition exists when at least one of the packet loss condition is registered or the operation of the apparatus including the first and second component is modified, the number of data packets received from a respective transmit facility are stored in a buffer or the sequence information included in the number of data packets is stored in the buffer, the buffer including a first part buffer and a second part buffer and the number of data packets or the sequence information being stored in the first part buffer until the first part buffer reaches a threshold occupancy and then being stored in the second part buffer, and wherein the processing circuitry is configured to cause the apparatus to evaluate the packet loss condition of the number of data packets received by the at least one of the at least two receive facilities by evaluating the number of data packets or the sequence information stored in the first part buffer upon or after a first test condition existing for testing packet loss condition, the first test condition existing when the first part buffer is full, the first part buffer being full being based on at least one of (i) at least one of a number of the number of data packets stored in the first part buffer or a total size of the number of data packets stored in the first part buffer or (ii) the sequence information stored in the first part buffer, and evaluating the number of data packets or the sequence information stored in the first part buffer and the second part buffer upon or after a second test condition existing for testing packet loss condition and after the first test condition existing for testing packet loss condition, the second test condition occurring upon either an elapsed time since the first test condition or at least one of (i) at least one of a number of the number of data packets stored in the second part buffer or a total size of the number of data packets stored in the second part buffer before the elapsed time since the first test condition or (ii) the sequence information stored in the second part buffer after the first test condition existing before the elapsed time since the first test condition.

8. The apparatus as claimed in claim 7, wherein at least one of (i) the apparatus is configured for use in medical imaging or (ii) the first component includes at least one imaging sensor.

9. A non-transitory computer-readable data medium including instructions for monitoring a data transmission between a first component and a second component that, when executed by processing circuitry, are configured to cause the processing circuitry to move one or more transmit facilities with respect to at least two receive facilities, the one or more transmit facilities being attached to the first component at a fixed position to and the at least two receive facilities being attached to the second component at a fixed position, and the move being a change in at least one of a position or an orientation of the one or more transmit facilities;

send a sequence of a number of consecutive data packets via a respective transmit facility of the one or more transmit facilities, each respective data packet of the sequence including sequence information, and the sequence information describing the position of the respective data packet in the sequence;

evaluate a packet loss condition of a number of data packets received by at least one of the at least two receive facilities, the evaluating being based on the sequence information of the number of data packets and the packet loss condition indicating that at least one of the data packets of the sequence was not received by any of the at least two receive facilities; and at least one of register a respective error for the respective receive facility in response to an error condition or modify an operation of an apparatus including the first component and the second component for the respective receive facility in response to the error condition, wherein the error condition for the respective receive facility is based on (1) location information relating to at least one of the position of the first component with regard to the second component or orientation of the first component with regard to the second component, and (2) at least one of (i) a measure for a receive quality of a signal or (ii) the number of data packets received from the respective transmit facility or from at least one of the one or more transmit facilities, the error condition exists when at least one of the packet loss condition is registered or the operation of the apparatus including the first and second component is modified, the number of data packets received from a respective transmit facility or at least the sequence information included in the number the data packets is stored in a buffer, the buffer including a first part buffer and a second part buffer and the number of data packets or the sequence information being stored in the first part buffer until the first part buffer reaches a threshold occupancy and then being stored in the second part buffer, and wherein the instructions for monitoring the data transmission between the first component and a second component, when executed by the processing circuitry, are configured to cause the processing circuitry to evaluate the packet loss condition of the number of data packets received by the at least one of the at least two receive facilities by evaluating the data packets or the sequence information stored in the first part buffer or the data packets upon or after a first test condition existing for testing packet loss condition, the first test condition existing when the first part buffer is full, the first part buffer being full being based on at least one of (i) at least one of a number of the number of data packets stored in the first part buffer or a total size of the number of data packets stored in the first part buffer or (ii) the sequence information stored in the first part buffer, and evaluating the data packets or the sequence information stored in the first part buffer and the second part buffer upon or after a second test condition existing for testing packet loss condition and after the first test condition existing for testing packet loss condition, the second test condition occurring upon either an elapsed time since the first test condition or at least one of (i) at least one of a number of the number of data packets stored in the second part buffer or a total size of the number of data packets stored in the second part buffer before the elapsed time since the first test condition or (ii) the sequence information stored in the second part buffer after the first test condition existing before the elapsed time since the first test condition.

* * * * *